United States Patent
Okamoto

(10) Patent No.: US 7,119,169 B2
(45) Date of Patent: Oct. 10, 2006

(54) RELA-ASSOCIATED INHIBITOR, PROCESS FOR PRODUCING THE SAME AND UTILIZATION THEREOF

(75) Inventor: Takashi Okamoto, Aichi (JP)

(73) Assignee: City of Nagoya, Aichi (JP)

( * ) Notice: Subject to any disclaimer, the term of this patent is extended or adjusted under 35 U.S.C. 154(b) by 80 days.

(21) Appl. No.: 10/374,055

(22) Filed: Feb. 27, 2003

(65) Prior Publication Data

US 2003/0148396 A1 Aug. 7, 2003

Related U.S. Application Data

(62) Division of application No. 09/857,447, filed as application No. PCT/JP99/06753 on Dec. 2, 1999, now Pat. No. 6,582,933.

(30) Foreign Application Priority Data

Dec. 3, 1998 (JP) .............................. P. 10-344038

(51) Int. Cl.
*A61K 38/16* (2006.01)

(52) U.S. Cl. ..................................... 530/358

(58) Field of Classification Search ................. 530/358
See application file for complete search history.

(56) References Cited

FOREIGN PATENT DOCUMENTS

WO WO 9631625 10/1996

OTHER PUBLICATIONS

Li et al. A new member of the I kappaB protein family, I kappaB epsilon, inhibits RelA (p65)-mediated NF-kappaB transcription Mol Cell Biol. Oct. 1997;17(10):6184-90.*
Hillier et al. GenBank Accession No. R55203 (May 1995).
Attwood, *Science*, 290(5491):471-473 (2000).
Skolnick et al, *Trends Biotechnol*, 18(1):34-39 (2000).
Metzler et al, *Nat. Struct. Biol.*, vol. 4. No. 7 (Jul. 1997).
Iwabuchi et al, *Proc. Natl. Acad. Sci., USA*.91(13):6098-6102 (1994).
Database Accession No. ai066638, "H. sapiens cDNA (EST) clone from fibroblasts" (Aug. 3, 1988), Abstract.
Database Accession No. w67935, "H. sapiens clone from fetal heart" (Jun. 16, 1996), Abstract.
Li et al, *Mol. and Cell. Biology*, 17(10):6184-6190 (1997).
Yang et al, *Proceedings of the Japanese Society for Immunology*, 28:Abstract 4-A8-261 (1998).
Yang et al, *The Journal of Biological Chemistry*, 274(22):15662-15670 (1999).
Lamerdin et al, *Genomics*, 34(0303):399-409 (1996).
Gorina et al, "Structure of the p53 Tumor Suppressor Bound to the Ankyrin and SH3 Domains of 53BP2", *Science*, vol. 274 (Nov. 8, 1996).
Ruben et al, Science, 251:1490-1493 (1991).
Ngo et al, *The Protein Folding Problem*, Birkhauser, Chapter 14, pp. 435-508 (1994).
Christmanson et al, *FEBS Letter*, 267(1):160-166 (1990).
Lodish et al, *Molecular Cell Biology*, W.H. Freeman & Co., New York, pp. 248-255 (1986).
GenBank Accession No. AA580180 (Nov. 1997).

* cited by examiner

*Primary Examiner*—Maher Haddad
(74) *Attorney, Agent, or Firm*—Sughrue Mion, PLLC

(57) ABSTRACT

Human RelA-associated inhibitor (RAI) comprises 351 amino acids and is capable of binding to p65, a subunit of the transcription factor NFκB. A process for producing RAI, a cDNA encoding it, a fragment capable of hybridizing selectively to the cDNA sequence, a plasmid for expression and duplication comprising the cDNA, a host cell transformed with the plasmid, an antibody against the polypeptide, a pharmaceutical composition comprising the polypeptide or the antibody against it and a method for diagnosis of diseases using the antibody against the RAI are disclosed.

1 Claim, 3 Drawing Sheets

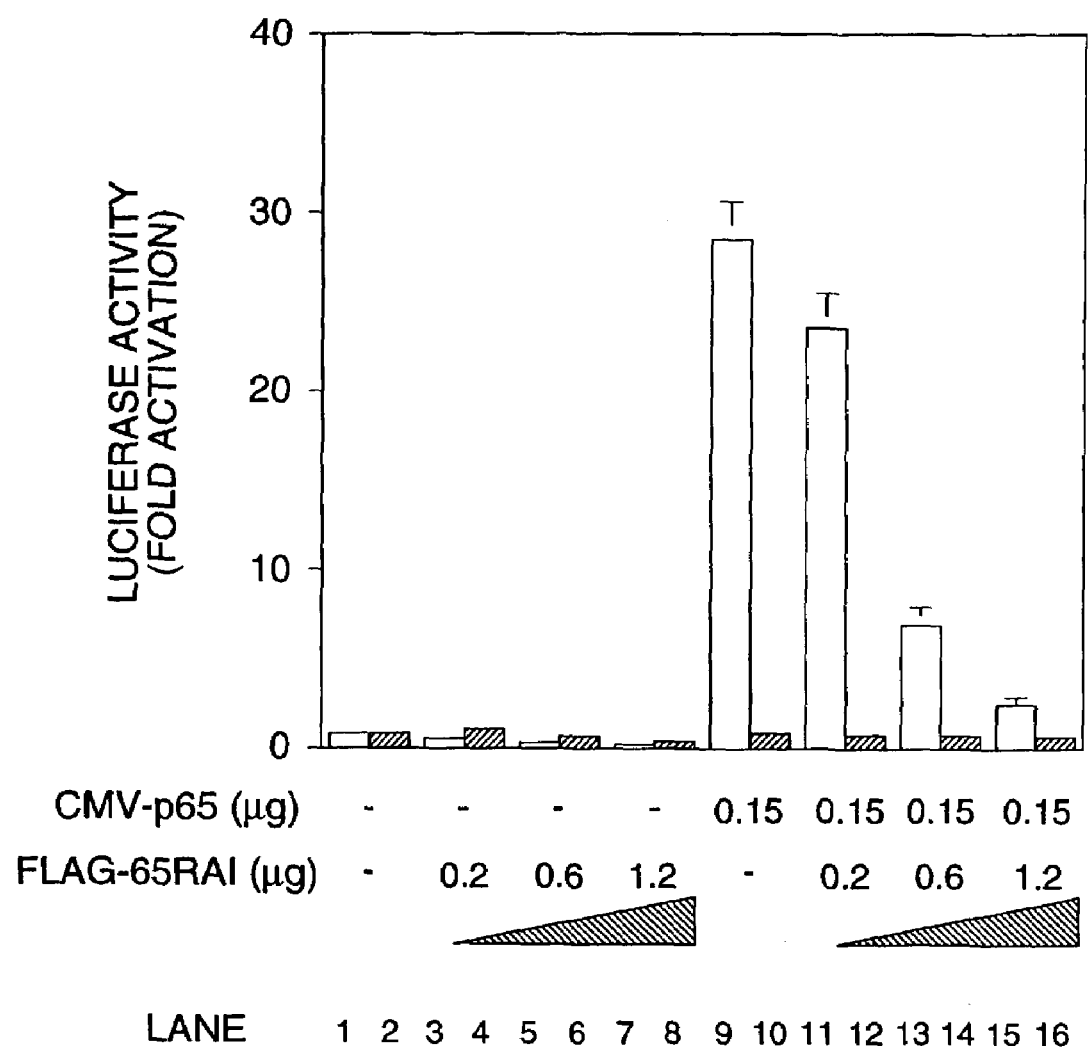

SEQUENCE LISTING

```
<160> NUMBER OF SEQ ID NOS: 11

<210> SEQ ID NO 1
<211> LENGTH: 351
<212> TYPE: PRT
<213> ORGANISM: Homo sapiens
<220> FEATURE:
<221> NAME/KEY: DOMAIN
<222> LOCATION: (145)..(174)
<223> OTHER INFORMATION: Ankyrin repeat
<220> FEATURE:
<221> NAME/KEY: DOMAIN
<222> LOCATION: (176)..(207)
<223> OTHER INFORMATION: Ankyrin repeat
<220> FEATURE:
<221> NAME/KEY: DOMAIN
<222> LOCATION: (209)..(241)
```

```
<223> OTHER INFORMATION: Ankyrin repeat
<220> FEATURE:
<221> NAME/KEY: DOMAIN
<222> LOCATION: (243)..(275)
<223> OTHER INFORMATION: Ankyrin repeat
<220> FEATURE:
<221> NAME/KEY: DOMAIN
<222> LOCATION: (287)..(338)
<223> OTHER INFORMATION: SH3 domain

<400> SEQUENCE: 1

Met Trp Met Lys Asp Pro Val Ala Arg Pro Leu Ser Pro Thr Arg Leu
1               5                   10                  15

Gln Pro Ala Leu Pro Pro Glu Ala Gln Ser Val Pro Glu Leu Glu Glu
            20                  25                  30

Val Ala Arg Val Leu Ala Glu Ile Pro Arg Pro Leu Lys Arg Arg Gly
        35                  40                  45

Ser Met Glu Gln Ala Pro Ala Val Ala Leu Pro Pro Thr His Lys Lys
    50                  55                  60

Gln Tyr Gln Gln Ile Ile Ser Arg Leu Phe His Arg His Gly Gly Pro
65              70                  75                  80

Gly Pro Gly Gly Arg Ser Gln Ser Cys Pro Pro Ser Leu Arg Asp Leu
                85                  90                  95

Arg Pro Gly Gln Gly Pro Leu Leu Pro His Gln Leu Pro Phe His
            100                 105                 110

Arg Pro Ala Pro Ser Gln Ser Ser Pro Pro Glu Gln Pro Gln Ser Met
        115                 120                 125

Glu Met Arg Ser Val Leu Arg Lys Ala Gly Ser Pro Arg Lys Ala Arg
    130                 135                 140

Arg Ala Arg Leu Asn Pro Leu Val Leu Leu Asp Ala Ala Leu Thr
145             150                 155                 160

Gly Glu Leu Glu Val Val Gln Gln Ala Val Lys Glu Met Asn Asp Pro
                165                 170                 175

Ser Gln Pro Asn Glu Glu Gly Ile Thr Ala Leu His Asn Ala Ile Cys
            180                 185                 190

Gly Ala Asn Tyr Ser Ile Val Asp Phe Leu Ile Thr Ala Gly Ala Asn
        195                 200                 205

Val Asn Ser Pro Asp Ser His Gly Trp Thr Pro Leu His Cys Ala Ala
    210                 215                 220

Ser Cys Asn Asp Thr Val Ile Cys Met Ala Leu Val Gln His Gly Ala
225             230                 235                 240

Ala Ile Phe Ala Thr Thr Leu Ser Asp Gly Ala Thr Ala Phe Glu Lys
                245                 250                 255

Cys Asp Pro Tyr Arg Glu Gly Tyr Ala Asp Cys Ala Thr Tyr Leu Ala
            260                 265                 270

Asp Val Glu Gln Ser Met Gly Leu Met Asn Ser Gly Ala Val Tyr Ala
        275                 280                 285

Leu Trp Asp Tyr Ser Ala Glu Phe Gly Asp Glu Leu Ser Phe Arg Glu
    290                 295                 300

Gly Glu Ser Val Thr Val Leu Arg Arg Asp Gly Pro Glu Glu Thr Asp
305             310                 315                 320

Trp Trp Trp Ala Ala Leu His Gly Gln Glu Gly Tyr Val Pro Arg Asn
                325                 330                 335

Tyr Phe Gly Leu Phe Pro Arg Val Lys Pro Gln Arg Ser Lys Val
            340                 345                 350
```

<210> SEQ ID NO 2
<211> LENGTH: 1053
<212> TYPE: DNA
<213> ORGANISM: Homo sapiens

<400> SEQUENCE: 2

| | | | | | |
|---|---|---|---|---|---|
| atgtggatga | aggaccctgt | agcaaggcct | ctcagcccca | cgaggctgca | gccagcactg | 60 |
| ccaccggagg | cacagtcggt | gcccgagctg | gaggaggtgg | cacgggtgtt | ggcggaaatt | 120 |
| ccccggcccc | tcaaacgcag | gggctccatg | gagcaggccc | ctgctgtggc | cctgccccct | 180 |
| acccacaaga | aacagtacca | gcagatcatc | agccgcctct | ccatcgtca | tgggggcca | 240 |
| gggcccgggg | gcggagcca | gagctgtccc | ccatcactga | gggatctgag | gccagggcag | 300 |
| ggcccctgc | tcctgcccca | ccagctccca | ttccaccgcc | cggccccgtc | ccagagcagc | 360 |
| ccaccagagc | agccgcagag | catggagatg | cgctctgtgc | tgcggaaggc | gggctcccg | 420 |
| cgcaaggccc | gccgcgcgcg | cctcaaccct | ctggtgctcc | tcctggacgc | ggcgctgacc | 480 |
| ggggagctgg | aggtggtgca | gcaggcggtg | aaggagatga | acgacccgag | ccagcccaac | 540 |
| gaggagggca | tcactgcctt | gcacaacgcc | atctgcggcg | ccaactactc | tatcgtggat | 600 |
| ttcctcatca | ccgcgggtgc | caatgtcaac | tcccccgaca | gccacggctg | gcacccttg | 660 |
| cactgcgcgg | cgtcgtgcaa | cgacacagtc | atctgcatgg | cgctggtgca | gcacggcgct | 720 |
| gcaatcttcg | ccaccacgct | cagcgacggc | gccaccgcct | tcgagaagtg | cgaccettac | 780 |
| cgcgagggtt | atgctgactg | cgccaccttac | ctggcagacg | tcgagcagag | tatggggctg | 840 |
| atgaacagcg | gggcagtgta | cgctctctgg | gactacagcg | ccgagttcgg | ggacgagctg | 900 |
| tccttccgcg | agggcgagtc | ggtcaccgtg | ctgcggaggg | acgggccgga | ggagaccgac | 960 |
| tggtggtggg | ccgcgctgca | cggccaggag | ggctacgtgc | cgcggaacta | cttcgggctg | 1020 |
| ttccccaggg | tgaagcctca | aaggagtaaa | gtc | | | 1053 |

<210> SEQ ID NO 3
<211> LENGTH: 2640
<212> TYPE: DNA
<213> ORGANISM: Homo sapiens

<400> SEQUENCE: 3

| | | | | | |
|---|---|---|---|---|---|
| ggaattcgcg | gccgcgtcga | caaacaagtg | agtctcggct | ggagtgcagt | ggtgcagtgg | 60 |
| tgcaatctcg | gctcactgca | acctccgcct | cctgggttca | agcgattcct | gtgcctcggc | 120 |
| cttccgagta | gctgggattg | caggcgtgtg | ccaccacgcc | cggctaattt | tttttttttt | 180 |
| tttttttttt | ttgtattttt | agtagagaca | gggttcttac | catgttggcc | aggctggtct | 240 |
| caaactcctg | atctcaagag | atgtggcctg | cctccggcct | cccaaagttc | tgggattaca | 300 |
| gggtgttgag | ccactctgac | tcagccaata | atgcatattt | ttatttccac | ctgctttact | 360 |
| gtcagaatga | gtaagacaga | gaagaaatca | ttaaacacca | ggattctact | tgcctgctgg | 420 |
| agttttctgc | ctgagatgtt | aggagaggaa | actctcagga | tctcagaaaa | tcacatctat | 480 |
| cacggttggt | agaagtagat | tctagagtca | gccagaatga | gttcaagtcc | caactgcatg | 540 |
| gctttgggca | actgactgtc | ctctctgagg | cccagattcc | ctttcggtaa | tgtggagatg | 600 |
| gcagtgtatc | tacctcacaa | agcagtggtg | agattacaat | aagtaggca | tgtaaagcgc | 660 |
| caggcacata | ctaactgctc | aataaatggg | aggcatcata | attgtatatt | attcacagcc | 720 |
| caaggaaagt | gtagcccaga | gagggcaagg | aacttgaccc | tgaggtcaac | acagaaaatc | 780 |
| atgtgctggt | tgtatgccct | ggaagttgtg | gagagggagt | gttgggtgtc | ttcctgggga | 840 |

```
cctgtcctct gatgggctct tgttccggct aggaccccc  aaaccccca ccgagctgga   900 gcctgagccg gagatagagg ggctgctgac accagtgctg gaggctggcg atgtggatga   960
aggaccctgt agcaaggcct ctcagcccca cgaggctgca gccagcactg ccaccggagg  1020
cacagtcggt gcccgagctg gaggaggtgg cacgggtgtt ggcggaaatt ccccggcccc  1080
tcaaacgcag gggctccatg gagcaggccc ctgctgtggc cctgccccct acccacaaga  1140
aacagtacca gcagatcatc agccgcctct tccatcgtca tggggggcca gggcccgggg  1200
ggcggagcca gagctgtccc ccatcactga gggatctgag gccagggcag ggcccctgc   1260 tcctgccca  ccagctccca ttccaccgcc cggcccgtc  ccagagcagc ccaccagagc  1320
agccgcagag catggagatg cgctctgtgc tgcggaaggc gggctcccg  cgcaaggccc  1380 gccgcgcgcg cctcaaccct ctggtgctcc tcctggacgc ggcgctgacc ggggagctgg  1440
aggtggtgca gcaggcggtg aaggagatga cgacccgag  ccagcccaac gaggagggca  1500
tcactgcctt gcaacgcc  atctgcgcg  ccaactactc tatcgtggat ttcctcatca  1560
ccgcgggtgc caatgtcaac tcccccgaca gccacggctg gacacccttg cactgcgcgg  1620
cgtcgtgcaa cgacacagtc atctgcatgg cgctggtgca gcacggcgct gcaatcttcg  1680
ccaccacgct cagcgacggc gccaccgcct tcgagaagtg cgacccttac cgcgagggtt  1740
atgctgactg cgccacctac ctggcagacg tcgagcagag tatggggctg atgaacagcg  1800 ggcagtgta  cgctctctgg gactacagcg ccgagttcgg ggacgagctg tccttccgcg  1860
agggcgagtc ggtcaccgtg ctgcggaggg acgggccgga ggagaccgac tggtggtggg  1920
ccgcgctgca cggccaggag ggctacgtgc cgcggaacta cttcgggctg ttccccaggg  1980
tgaagcctca aaggagtaaa gtctagcagg atagaaggag gtttctgagg ctgacagaaa  2040
caagcattcc tgccttccct ccagacctct ccctctgttt tttgctgcct ttatctgcac  2100
ccctcaccct gctggtggtg gtccttgcca ccggttctct gttctcctgg aagtccaggg  2160
aagaaggagg gccccagcct taaatttagt aatctgcctt agccttggga ggtctgggaa  2220
gggctggaaa tcactgggga caggaaacca cttcctttgt ccaaatcaga tcccgtccaa  2280
agtgcctccc atgcctacca ccatcatcac atcccccagc aagccagcca cctgcccagc  2340
cgggcctggg atgggccacc acaccactgg atattcctgg gagtcactgc tgacaccatc  2400
tctcccagca gtcttggggt ctgggtggga acattggtc  tctaccagga tccctgcccc  2460
acctctcccc aattaagtgc cttcacacag cactggttta atgtttataa acaaaataga  2520
gaaactttcc ttataaataa aagtagtttg cacagaaaaa aaaaaacac  aaccttcggc  2580 cgccccacca agctctgtct ccaaaaaaaa aaaaaaaaa  aaaaaactc  gagagttcta  2640
```

<210> SEQ ID NO 4
<211> LENGTH: 2640
<212> TYPE: DNA
<213> ORGANISM: Homo sapiens
<220> FEATURE:
<221> NAME/KEY: exon
<222> LOCATION: (951)..(2003)
<223> OTHER INFORMATION:

<400> SEQUENCE: 4

```
ggaattcgcg gccgcgtcga caaacaagtg agtctcggct ggagtgcagt ggtgcagtgg    60
tgcaatctcg gctcactgca acctccgcct cctgggttca gcgattcct  gtgcctcggc   120 cttccgagta gctgggattg caggcgtgtg ccaccacgcc cggctaattt tttttttttt   180
tttttttttt ttgtattttt agtagagaca gggttcttac catgttggcc aggctggtct   240
```

-continued

```
caaactcctg atctcaagag atgtggcctg cctccggcct cccaaagttc tgggattaca      300
gggtgttgag ccactctgac tcagccaata atgcatattt ttatttccac ctgctttact      360
gtcagaatga gtaagacaga gaagaaatca ttaaacacca ggattctact tgcctgctgg      420
agttttctgc ctgagatgtt aggagaggaa actctcagga tctcagaaaa tcacatctat      480
cacggttggt agaagtagat tctagagtca gccagaatga gttcaagtcc caactgcatg      540
gctttgggca actgactgtc ctctctgagg cccagattcc ctttcggtaa tgtggagatg      600
gcagtgtatc tacctcacaa agcagtggtg agattacaat aaggtaggca tgtaaagcgc      660
caggcacata ctaactgctc aataaatggg aggcatcata attgtatatt attcacagcc      720
caaggaaagt gtagcccaga gagggcaagg aacttgaccc tgaggtcaac acagaaaatc      780
atgtgctggt tgtatgccct ggaagttgtg gagagggagt gttgggtgtc ttcctgggga      840
cctgtcctct gatgggctct tgttccggct aggacccccc aaaccccccca ccgagctgga      900 gcctgagccg gagatagagg ggctgctgac accagtgctg gaggctggcg atg tgg         956
                                                             Met Trp
                                                              1
```

```
atg aag gac cct gta gca agg cct ctc agc ccc acg agg ctg cag cca       1004
Met Lys Asp Pro Val Ala Arg Pro Leu Ser Pro Thr Arg Leu Gln Pro
        5                   10                  15 gca ctg cca ccg gag gca cag tcg gtc ccc gag ctg gag gag gtg gca       1052
Ala Leu Pro Pro Glu Ala Gln Ser Val Pro Glu Leu Glu Glu Val Ala
 20                  25                  30 cgg gtg ttg gcg gaa att ccc cgg ccc ctc aaa cgc agg ggc tcc atg       1100
Arg Val Leu Ala Glu Ile Pro Arg Pro Leu Lys Arg Arg Gly Ser Met
 35                  40                  45                  50 gag cag gcc cct gct gtg gcc ctg ccc cct acc cac aag aaa cag tac       1148
Glu Gln Ala Pro Ala Val Ala Leu Pro Pro Thr His Lys Lys Gln Tyr
                 55                  60                  65 cag cag atc atc agc cgc ctc ttc cat cgt cat ggg ggg cca ggg ccc       1196
Gln Gln Ile Ile Ser Arg Leu Phe His Arg His Gly Gly Pro Gly Pro
         70                  75                  80 ggg ggg cgg agc cag agc tgt ccc cca tca ctg agg gat ctg agg cca       1244
Gly Gly Arg Ser Gln Ser Cys Pro Pro Ser Leu Arg Asp Leu Arg Pro
     85                  90                  95 ggg cag ggc ccc ctg ctc ctg ccc cac cag ctc cca ttc cac cgc ccg       1292
Gly Gln Gly Pro Leu Leu Leu Pro His Gln Leu Pro Phe His Arg Pro
100                 105                 110 gcc ccg tcc cag agc agc cca cca gag cag ccg cag agc atg gag atg       1340
Ala Pro Ser Gln Ser Ser Pro Pro Glu Gln Pro Gln Ser Met Glu Met
115                 120                 125                 130 cgc tct gtg ctg cgg aag gcg ggc tcc ccg cgc aag gcc cgc cgc gcg       1388
Arg Ser Val Leu Arg Lys Ala Gly Ser Pro Arg Lys Ala Arg Arg Ala
                135                 140                 145 cgc ctc aac cct ctg gtg ctc ctc gac gcg gcg ctg acc ggg gag           1436
Arg Leu Asn Pro Leu Val Leu Leu Asp Ala Ala Leu Thr Gly Glu
            150                 155                 160 ctg gag gtg gtg cag cag gcg gtg aag gag atg aac gac ccg agc cag       1484
Leu Glu Val Val Gln Gln Ala Val Lys Glu Met Asn Asp Pro Ser Gln
        165                 170                 175 ccc aac gag gag ggc atc act gcc ttg cac aac gcc atc tgc ggc gcc       1532
Pro Asn Glu Glu Gly Ile Thr Ala Leu His Asn Ala Ile Cys Gly Ala
    180                 185                 190 aac tac tct atc gtg gat ttc ctc atc acc gcg ggt gcc aat gtc aac       1580
Asn Tyr Ser Ile Val Asp Phe Leu Ile Thr Ala Gly Ala Asn Val Asn
195                 200                 205                 210
```

-continued

| | | | | | | | | | | | | | | | | |
|---|---|---|---|---|---|---|---|---|---|---|---|---|---|---|---|---|
| tcc | ccc | gac | agc | cac | ggc | tgg | aca | ccc | ttg | cac | tgc | gcg | gcg | tcg | tgc | 1628 |
| Ser | Pro | Asp | Ser | His | Gly | Trp | Thr | Pro | Leu | His | Cys | Ala | Ala | Ser | Cys | |
| | | | 215 | | | | 220 | | | | | 225 | | | | |

| | | | | | | | | | | | | | | | | |
|---|---|---|---|---|---|---|---|---|---|---|---|---|---|---|---|---|
| aac | gac | aca | gtc | atc | tgc | atg | gcg | ctg | gtg | cag | cac | ggc | gct | gca | atc | 1676 |
| Asn | Asp | Thr | Val | Ile | Cys | Met | Ala | Leu | Val | Gln | His | Gly | Ala | Ala | Ile | |
| | | 230 | | | | | 235 | | | | | 240 | | | | |

| | | | | | | | | | | | | | | | | |
|---|---|---|---|---|---|---|---|---|---|---|---|---|---|---|---|---|
| ttc | gcc | acc | acg | ctc | agc | gac | ggc | gcc | acc | gcc | ttc | gag | aag | tgc | gac | 1724 |
| Phe | Ala | Thr | Thr | Leu | Ser | Asp | Gly | Ala | Thr | Ala | Phe | Glu | Lys | Cys | Asp | |
| | | | 245 | | | | | 250 | | | | | 255 | | | |

| | | | | | | | | | | | | | | | | |
|---|---|---|---|---|---|---|---|---|---|---|---|---|---|---|---|---|
| cct | tac | cgc | gag | ggt | tat | gct | gac | tgc | gcc | acc | tac | ctg | gca | gac | gtc | 1772 |
| Pro | Tyr | Arg | Glu | Gly | Tyr | Ala | Asp | Cys | Ala | Thr | Tyr | Leu | Ala | Asp | Val | |
| | | 260 | | | | | 265 | | | | | 270 | | | | |

| | | | | | | | | | | | | | | | | |
|---|---|---|---|---|---|---|---|---|---|---|---|---|---|---|---|---|
| gag | cag | agt | atg | ggg | ctg | atg | aac | agc | ggg | gca | gtg | tac | gct | ctc | tgg | 1820 |
| Glu | Gln | Ser | Met | Gly | Leu | Met | Asn | Ser | Gly | Ala | Val | Tyr | Ala | Leu | Trp | |
| 275 | | | | | 280 | | | | | 285 | | | | | 290 | |

| | | | | | | | | | | | | | | | | |
|---|---|---|---|---|---|---|---|---|---|---|---|---|---|---|---|---|
| gac | tac | agc | gcc | gag | ttc | ggg | gac | gag | ctg | tcc | ttc | cgc | gag | ggc | gag | 1868 |
| Asp | Tyr | Ser | Ala | Glu | Phe | Gly | Asp | Glu | Leu | Ser | Phe | Arg | Glu | Gly | Glu | |
| | | | | 295 | | | | | 300 | | | | | 305 | | |

| | | | | | | | | | | | | | | | | |
|---|---|---|---|---|---|---|---|---|---|---|---|---|---|---|---|---|
| tcg | gtc | acc | gtg | ctg | cgg | agg | gac | ggg | ccg | gag | gag | acc | gac | tgg | tgg | 1916 |
| Ser | Val | Thr | Val | Leu | Arg | Arg | Asp | Gly | Pro | Glu | Glu | Thr | Asp | Trp | Trp | |
| | | | 310 | | | | | 315 | | | | | 320 | | | |

| | | | | | | | | | | | | | | | | |
|---|---|---|---|---|---|---|---|---|---|---|---|---|---|---|---|---|
| tgg | gcc | gcg | ctg | cac | ggc | cag | gag | ggc | tac | gtg | ccg | cgg | aac | tac | ttc | 1964 |
| Trp | Ala | Ala | Leu | His | Gly | Gln | Glu | Gly | Tyr | Val | Pro | Arg | Asn | Tyr | Phe | |
| | | 325 | | | | | 330 | | | | | 335 | | | | |

| | | | | | | | | | | | | |
|---|---|---|---|---|---|---|---|---|---|---|---|---|
| ggg | ctg | ttc | ccc | agg | gtg | aag | cct | caa | agg | agt | aaa | gtc | tagcaggata | 2013 |
| Gly | Leu | Phe | Pro | Arg | Val | Lys | Pro | Gln | Arg | Ser | Lys | Val | | |
| | | | 340 | | | | | 345 | | | | 350 | | | gaaggaggtt tctgaggctg acagaaacaa gcattcctgc cttccctcca gacctctccc 2073 tctgtttttt gctgccttta tctgcacccc tcaccctgct ggtggtggtc cttgccaccg 2133 gttctctgtt ctcctggaag tccagggaag aaggagggcc ccagccttaa atttagtaat 2193 ctgccttagc cttgggaggt ctgggaaggg ctggaaatca ctggggacag gaaaccactt 2253 cctttttgcca aatcagatcc cgtccaaagt gcctcccatg cctaccacca tcatcacatc 2313 ccccagcaag ccagccacct gcccagccgg gcctgggatg gccaccaca ccactgata 2373 ttcctgggag tcactgctga caccatctct cccagcagtc ttggggtctg ggtgggaaac 2433 attggtctct accaggatcc ctgccccacc tctccccaat taagtgcctt cacacagcac 2493 tggtttaatg tttataaaca aaatagagaa actttcctta taaataaaag tagtttgcac 2553 agaaaaaaaa aaaacacaac cttcggccgc cccaccaagc tctgtctcca aaaaaaaaaa 2613 aaaaaaaaaa aaaactcgag agttcta 2640

<210> SEQ ID NO 5
<211> LENGTH: 27
<212> TYPE: DNA
<213> ORGANISM: Artificial Sequence
<220> FEATURE:
<223> OTHER INFORMATION: Forward primer containing BamHI restriction
      site

<400> SEQUENCE: 5
ggcggatccc tccgcctgcc gcctgtc                                        27

<210> SEQ ID NO 6
<211> LENGTH: 27
<212> TYPE: DNA
<213> ORGANISM: Artificial Sequence
<220> FEATURE:
<223> OTHER INFORMATION: Reverse primer containing BamHI restriction
      site

```
<400> SEQUENCE: 6
gctggatccg gggcaggggc tggagcc                                    27

<210> SEQ ID NO 7
<211> LENGTH: 30
<212> TYPE: DNA
<213> ORGANISM: Artificial Sequence
<220> FEATURE:
<223> OTHER INFORMATION: Forward primer containing SalI restriction site

<400> SEQUENCE: 7
caatggtcga catggatctg actcttgctg                                 30

<210> SEQ ID NO 8
<211> LENGTH: 30
<212> TYPE: DNA
<213> ORGANISM: Artificial Sequence
<220> FEATURE:
<223> OTHER INFORMATION: Reverse primer containing BamHI restriction
      site

<400> SEQUENCE: 8
gatcaggatc ctcaggccaa gctcctttgt                                 30

<210> SEQ ID NO 9
<211> LENGTH: 27
<212> TYPE: DNA
<213> ORGANISM: Artificial Sequence
<220> FEATURE:
<223> OTHER INFORMATION: Forward primer F132 containing EcoRI
      restriction site

<400> SEQUENCE: 9
gcttcgaatt ctgtgctgcg gaaggcg                                    27

<210> SEQ ID NO 10
<211> LENGTH: 30
<212> TYPE: DNA
<213> ORGANISM: Artificial Sequence
<220> FEATURE:
<223> OTHER INFORMATION: Reverse primer F132 containing BamHI
      restriction site

<400> SEQUENCE: 10
gatcaggatc ctcaggccaa gctcctttgt                                 30

<210> SEQ ID NO 11
<211> LENGTH: 22
<212> TYPE: DNA
<213> ORGANISM: Artificial Sequence
<220> FEATURE:
<223> OTHER INFORMATION: Oct-consensus sequence of kB sequence

<400> SEQUENCE: 11
tgtcgaatgc aaatcactag aa                                         22
```

RELA-ASSOCIATED INHIBITOR, PROCESS FOR PRODUCING THE SAME AND UTILIZATION THEREOF

CROSS-REFERENCE TO RELATED APPLICATIONS

This application is a Divisional of U.S. application Ser. No. 09/857,447, filed Jun. 4, 2001 (now U.S. Pat. No. 6,582.933); which is a 371 of PCT/JP99/06753, filed Dec. 2, 1999, the disclosure of each of which is incorporated herein by reference.

TECHNICAL FIELD

The present invention relates to a protein that inhibits activation of transcription factor NFκB.

More detailed, the present invention relates to p65-binding protein (called RelA-associated inhibitor or abbreviated as RAI hereinafter) that binds to p65, which is a submit of transcription factor NFκB, and that inhibits transcriptional activity of NFκB, a process for producing it, a cDNA encoding it, a vector comprising the cDNA, a host cell transformed with the vector, an antibody against the inhibitor, and a pharmaceutical composition comprising the inhibitor or the antibody.

Further, the present invention relates to recombinant production of these proteins (especially, in vivo production), a nucleotide encoding them, a vector for expression and duplication and treatment and/or prevention of adult respiratory distress syndrome (ARDS), asthma, Allograft rejection, inflammatory diseases (inflammatory arthritis, angitis etc.), ischemic diseases, autoimmune diseases including chronic rheumatism, metastasis and invasion of cancer, vasoreconstriction and diseases induced by NFκB besides above.

TECHNICAL BACKGROUND

An acceleration of expressing many and various genes is observed in inflammation. Such genes include ones encoding interleukin, transcription factors, cohesive molecules, and factors in coagulation system etc. NFκB which is a transcription factor has been said to relate to the transcription of such genes mostly.

It has been known that transcription factor NFκB is expressed in cytoplasm. The transcription and induction of gene due to NFκB-like proteins may be caused by activation of the protein. By such an activation, it becomes possible to translocate the transcription factor prepared in advance from cytoplasm to nucleus.

It is known that this translocation is controlled by phosphorylation and degradation of suppressor protein which is called for IκB.

Transcription factor NFκB was isolated from matured B cells in the form of binding to 10 nucleotide sequence mochief in κ light chain enhancer for the first time. Therefore, NFκB was thought to be specific for the generating stage of matured B cells. However, NFκB-like proteins have been identified in a lot of cells, so it is shown that such a factor relates to induction of gene transcription generally. Such fact has been confirmed by functional identification of an active type NFκB-binding position in some inducing genes.

NFκB is a heterodimer consisting of a submit of 50 kDa (p50) and a submit of 65 kDa (p65).

NF kappa B (NFκB), which is a nuclear factor, is a sequence-specific DNA-binding protein complex which regulates the expression of viral genomes, including the human immunodeficiency virus (HIV), and a variety of cellular genes, particularly those involved in immune and inflammatory responses. The members of the NFκB family in mammalian cells include the proto-oncogene c-Rel, p50/p105 (NFκB1), p65 (RelA), p52/p100 (NFκB2), and RelB etc.

All of these proteins share a conserved 300 amino acid region of homology known as the Rel homology domain (RHD), which is responsible for DNA binding, dimerization, and nuclear translocation of NFκB.

In most cells, Rel family members can form hetero- and homodimers with distinct specificities in various combinations. A common feature of the regulation of transcription factors belonging to Rel family is their sequestration in the cytoplasm as inactive complexes with a class of inhibitory molecules known as IKBs. Treatment of cells with a variety of inducers such as phorbol esters, intedeukin 1, tumor necrosis factor-α (TNF-α), viral infection and many mitogens and cytokines etc. results in the dissociation of the cytoplasmic complexes and translocation of free NFκB into the nucleus. The dissociation of the cytoplasmic complexes is known to be triggered by the phosphorylation and subsequent degradation of the IKB proteins. Such a degradation exposes the nuclear localization sequence in the remaining NFκB heterodimer, leading to nuclear translocation and subsequent binding of NFκB to DNA regulatory elements within NFκB target genes. The p65 submit is frequently detected in NFκB complexes and has a strong transcription activation potential. p65 dimerizes with other NFκB family members and activates gene expression via its potent transactivation domain.

DISCLOSURE OF THE INVENTION

The object of the present invention is to provide a novel protein that inhibits transcriptional activity of NFκB (NFκB inhibitor), a process for producing it, a cDNA encoding it, a vector comprising the cDNA, a host cell transformed with the vector, an antibody against the inhibitor, and a pharmaceutical composition comprising the inhibitor or the antibody.

The present inventor et al. have thought that novel inhibitors may exist besides IκB which was known as an NFκB inhibitor. From the result of focusing their attention on and an extensive studies of NFκB, especially p65 submit, the present inventor et al. have achieved to find out a novel NFκB inhibitor, confirmed amino acid sequence, a cDNA sequnce encoding it, function of the inhibitor and tissue-distribution etc. and then completed the present invention.

RelA-associated inhibitor of the present invention is regarded as nucleus factor and inhibits NFκB-dependent transcription activation by inhibiting DNA-binding activity of NFκB. The gene encodes RelA-associated inhibitor is a gene having a high homology to the C-terminal region of 53BP2 containing four consecutive ankyrin repeats and an SH3 domain.

RAI appeared to locate in nucleus with the same location pattern of TNF-α-induced p65. In addition, RAI inhibits activation of NFκB, but does not show any influence on p53-dependent transcription activation in the cells which is transformed temporarily. Therefore, RAI is a novel p65-binding protein which relates to another mechanism of NFκB-dependent transcription regulation. The present inventor has confirmed these interaction in vitro with bacterially expressed fusion proteins and in vivo using immunoprecipitation/Western blot assay.

In spite of its similarity to 53BP2, RAI did not shown any interaction with p53 in a yeast two-hybrid assay. The cDNA encodes this protein has a high structual homology to 200 amino acid at the C-terminal region of 53BP2 containing four ankyrin repeats and an SH3 domain that are important for protein-protein interactions.

In human, mRNA of RAI was specifically expressed in heart, placenta and prostate while it was markedly reduced in liver, skeletal muscle and peripheral blood leukocyte.

Recent rapid developments in techniques for constructing cDNAs and sequencing techniques have made it possible to quickly sequence a large amount of cDNAs. By utilizing these techniques, a process, which comprises constructing cDNAs library from various cells or tussles, cloning cDNAs at random, identifying the nucleotide sequences thereof, expressing novel polypeptides encoded by them to analyze its physiological function, is now in progress. Method of yeast two-hybridization has been known as one of such techniques.

By this technique, it becomes possible to identify a large amount of homologous proteins at the same time and to obtain the aimed protein only easily by inserting reporter genes such as fluorescent marker etc.

The present inventor has carried out experiments of such a yeast two-hybrid screen using NFκB protein submit p65 as a probe to find a novel factor that binds to a novel p65 and that inhibits an activity of p65 and then found out the factor of the present invention.

The sequence of RelA-associated inhibitor of the present invention has been confirmed to be novel according to a homology search. Only a sequence of RelA-associated inhibitor of the present invention is a novel one among some clones obtained by the process for the sequence of the present invention described hereinafter.

The amino acid sequence of RelA-associated inhibitor of the present invention is as shown in SEQ ID NO. 1. This amino acid sequnce contains four ankyrin repeats and an SH3 domain, so it is regarded as a member of Rel family.

The present invention relates to
(1) a RelA-associated inhibitor comprising amino acid sequence shown in SEQ ID NO. 1,
(2) a cDNA encoding the RelA-associated inhibitor described above (1),
(3) a cDNA comprising a nucleotide sequence shown in SEQ ID NO. 2, and
(4) a cDNA comprising a nucleotide sequence shown in SEQ ID NO. 3.

BRIEF DESCRIPTION OF FIGURES

FIG. 3 shows a dose-dependent inhibition manner of RAI on NFκB-dependent transcription activation. The activity of activating p65-induced transcription in case of non-expression of RAI is represented by luciferase activity at lane 9. Such an action is inhibited by RAI expression in a dose-dependent manner (lane 11, lanes 13 and 15).

DETAILED DESCRIPTION OF THE INVENTION

Figure 1:
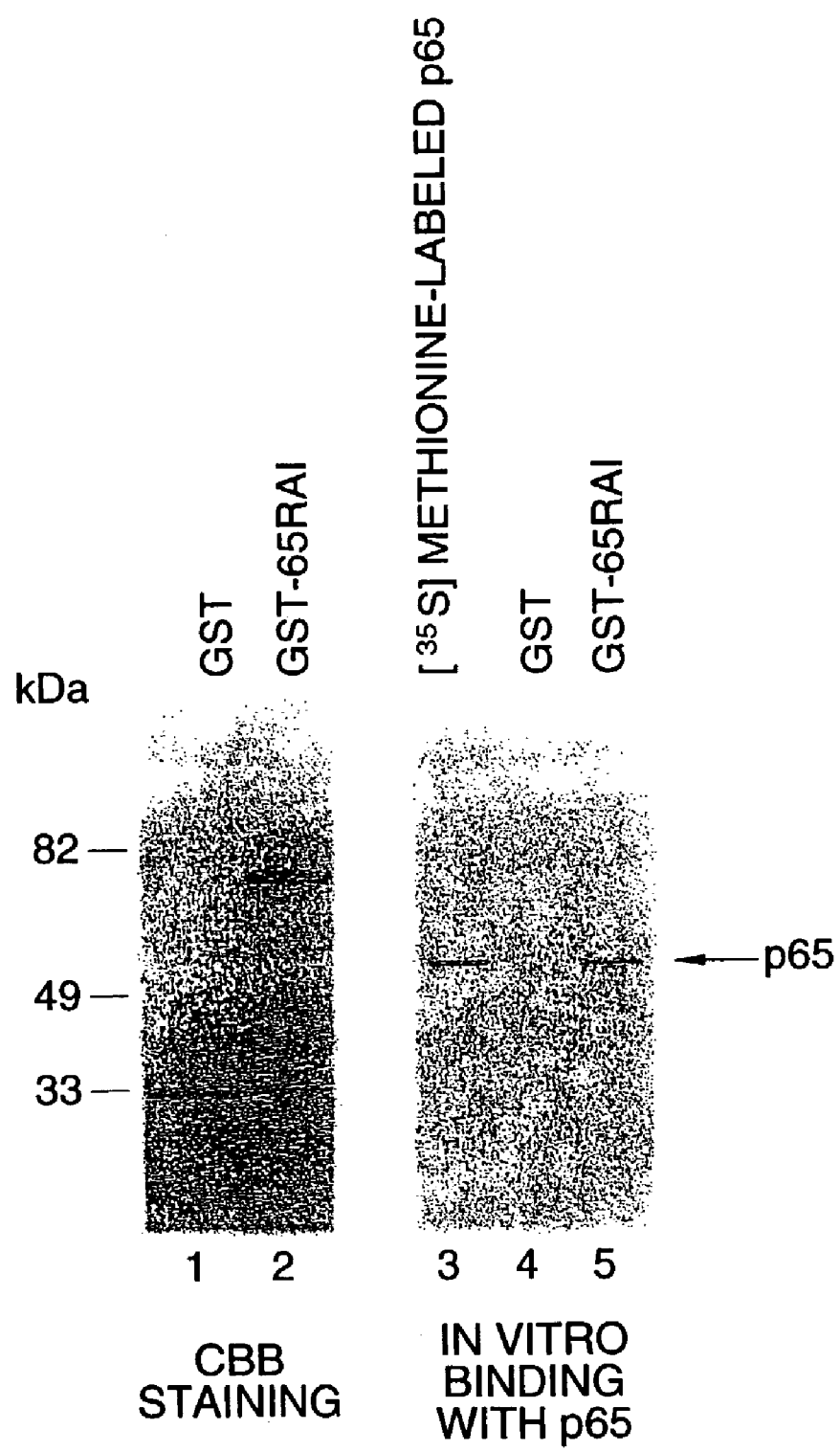
FIG. 1 shows the results of analyses of GST and GST-RAI fusion proteins, which were expressed in *E. coli*, on SDS-PAGE with CBB staining (lanes 1 and 2) and analyses of the said proteins by autoradiography after protting labeled p65 (lanes 3–5). One tenth of amount of labeled p65 at lane 5 was used at lane 3.

The present invention relates to a RelA-associated inhibitor comprising an amino acid sequence shown in SEQ ID NO. 1 in substantially purified form, a homologue thereof, a fragment of the sequence and a homologue of the fragment.

Further, the present invention relates to cDNAs encoding the above RelA-associated inhibitor. More particularly, the present invention relates to cDNAs comprising nucleotide sequences shown in SEQ ID NOS. 2 or 3 and cDNA containing a fragment capable of hybridizing selectively to nucleotide sequences shown in SEQ ID NOS. 2 or 3.

A RelA-associated inhibitor of the present invention comprising an amino acid sequence shown in SEQ ID NO. 1 in substantially purified form will generally comprise the polypeptide in a preparation in which more than 90%, e.g. 95%, 98% or 99% of the polypeptide in the preparation is that of the SEQ ID NO. 1.

A homologue of RelA-associated inhibitor of the present invention comprising an amino acid sequence shown in SEQ ID NO. 1 will be generally at least 70%, preferably at least 80 or 90% and more preferably at least 95% homologous to the polypeptide comprising the said amino acid sequence over a region of at least 20, preferably at least 30, for instance 40, 60 or 100 more contiguous amino acids. Such a polypeptide homologue will be referred to a RelA-associated inhibitor of the present invention.

In addition, a fragment of RelA-associated inhibitor of the present invention comprising an amino acid sequence shown in SEQ ID NO. 1 or its homologues will be at least 10, preferably at least 15, for example, 20, 25, 30, 40, 50 or 60 amino acids in length.

A cDNA capable of selectively hybridizing to the cDNA comprising nucleotide sequences shown in SEQ ID NOS. 2 or 3 will be generally at least 70%, preferably at least 80 or 90% and more preferably at least 95% homologous to the cDNA comprising the said nucleotide sequence over a region of at least 20, preferably at least 30, for instance 40, 60 or 100 or more contiguous nucleotides. Such a cDNA will be referred to "a cDNA of the present invention". A cDNA capable of selectively hybridizing to the cDNA also includes cohesive sequence. The condition for hybridizing is preferably stringent one.

Fragments of the cDNA comprising nucleotide sequences shown in SEQ ID NOS. 2 or 3 will be at least 10, preferably at least 15, for example, 20, 25, 30 or 40 nucleotides in length, and will be also referred to "a cDNA of the present invention" as used herein.

A further embodiment of the present invention provides replication and expression vectors carrying cDNA of the present invention. The vectors may be, for example, plasmid, virus or phage vectors provided with an origin of replication, optionally a promoter for the expression of the said cDNA and optionally a regulator of the promoter. The vector may contain one or more selectable marker genes, for example, a luciferase expression gene or an ampicillin resistance gene. The vector may be used in vitro, for example, of the production of RNA corresponding to the cDNA, or used to transfect a host cell.

A further embodiment of the present invention provides host cells transformed with the vectors for the replication and expression of the cDNA of the present invention, including the cDNA comprising nucleotide sequences shown in SEQ ID NOS. 2 or 3 or the open reading frame thereof. The cells will be chosen to be compatible with the vector and may for example, be bacterial, yeast, insect cells or mammalian cells.

A further embodiment of the present invention provides a process for producing a RelA-associated inhibitor which comprises culturing host cells of the present invention under conditions effective to express a RelA-associated inhibitor of the present invention. Preferably, in addition, such a process is carried out under conditions in which the polypeptide of the present invention is expressed and then produced from the host cells.

cDNA of the present invention may also be inserted into the vectors described above in an antisense orientation in order to prove for the production of antisense. Such antisense may be used in a method of controlling the levels of a polypeptide of the present invention in a cell.

The invention also provides monoclonal or polyclonal antibodies against a RelA-associated inhibitor of the present invention. The invention further provides a process for the production of monoclonal or polyclonal antibodies to the RelA-associated inhibitor of the present invention. Monoclonal antibodies may be prepared by common hybridoma technology using RelA-associated inhibitor of the present invention or fragments thereof, as an immunogen. Polyclonal antibodies may also be prepared by common means which comprise inoculating host animals, (for example, a rat or a rabbit etc.), with RelA-associated inhibitor of the present invention and recovering immune serum.

The present invention also provides pharmaceutical compositions comprising a RelA-associated inhibitor of the present invention, or an antibody thereof, in association with a pharmaceutically acceptable diluent and/or carrier.

The present invention also provides a method for diagnosis of diseases etc. induced by NFκB using an antibody against a RelA-associated inhibitor of the present invention. The various methods for diagnosis using such an antibody have been known. For example, it may be carried out by determination of amount of enzyme according to EIA method etc. using an antigen-antibody reaction.

The RelA-associated inhibitor of the present invention specified in (1) includes that which a part of their amino acid sequence is lacking (e.g., a polypeptide comprised of the only essential sequence for revealing a biological activity in amino acid sequence shown in SEQ ID NO. 1), that which a part of their amino acid sequence is replaced by other amino acids (e.g., those replaced by amino acid having a similar property) and that which other amino acids are added or inserted into a part of their amino acid sequence, as well as those comprising the amino acid sequence shown in SEQ ID NO. 1.

As known well, there are one to six kinds of codon as that encoding one amino acid (for example, one kind of codon for Methionine (Met), and six kinds of codon for Leucine (Leu) are known). Accordingly, the nucleotide sequence of cDNA can be changed in order to encode the polypeptide having the same amino acid sequence.

The cDNA of the present invention, specified in (2) includes a group of every nucleotide sequence encoding RelA-associated inhibitor in (1) shown in SEQ ID NO. 1. There is a probability that yield of a RelA-associated inhibitor is improved by changing a nucleotide sequence.

The cDNA specified in (3) is the embodiment of the cDNA shown in (2), and indicate the sequence of natural form.

The cDNA shown in (4) indicates the sequence of the cDNA specified in (3) with natural non-translational region.

(5) Sequnces shown in SEQ ID NO. 4 reveal the correspondence between cDNA sequence in (4) shown in SEQ ID NO. 3 and amino acid sequence shown in (1).

cDNA carrying nucleotide sequence shown in SEQ ID NO. 3 and RelA-associated inhibitor comprising amino acid sequnce shown in SEQ ID NO. 1 of the present invention may be prepared by the following method:

1) Identification of the protein capable for interacting on p65 may be carried out by yeast two-hybridization method.

The central part of p65 (possessing properties comprising a dimer domain, nucleus translocatin signal and multiple proline) is cloning into plasmid (pAS2-1 etc.) to contain yeast GAL4-binding domain in the same frame.

2) Human (placenta, brain etc.) cDNA library constructed in GAL4 transcription activating domain vector pACT2 is cloned using the obtained plasmid as a probe.

The yeast tranformats are obtained by screening using yeast (Y190 strain etc.). From them, clones which are incubated on the culture for selection are screened according to blue-colouring by filter-lift-glactosidase assay.

3) Rescreening is carried out using alternative yeast (Y187 strain etc.) to confirm plasmid clone capable for interacting p65 probe specifically. It is possible to identify these clones according to both strands DNA sequencing.

4) The clones encoding RelA-associated inhibitor of the present invention may be obtained from the obtained clones by removing known ones.

5) Aimed full-length cDNA of about 6 kbp may be isolated by plaque-hybridization using the obtained DNA fragment from human library (placenta, brain etc.).

6) RelA-associated inhibitor of the present invention may be prepared from the isolated cDNA using expression cells (CHO cell, COS cell etc.) according to known methods.

Apart from the ankyrin repeats and SH3 domain, the RAI sequence is unrelated to that of any protein in current databases using BLAST research.

It is necessary to confirm whether the full-length or almost full-length cDNA has been obtained. It has been confirmed that the obtained cDNA is almost full-length by Northern blot analysis according to comparison with size of the obtained mRNA.

Once the nucleotide sequences shown in SEQ ID NOS. 2 and 3 are determined, cDNAs of the present invention are obtained by chemical synthesis, or by hybridization making use of nucleotide fragments which are chemically synthesized as a probe. Furthermore, cDNAs of the present invention may be obtained in desired amount by transforming a vector that contains the cDNA into a proper host, and culturing the transformant.

The polypeptides of the present invention may be prepared by:

(1) isolating and purifying from an organism or a cultured cell, (2) chemically synthesizing, or (3) using recombinant DNA technology etc., preferably, by the method described in (3) in an industrial production.

Examples of expression system (host-vector system) for producing a polypeptide by using recombinant DNA technology are the expression systems of bacteria, yeast, insect cells and mammalian cells.

In the expression of the polypeptide, for example, in *E. Coli*, the expression vector may be prepared by adding the initiation codon (ATG) to 5' end of a cDNA encoding mature peptide, connecting the cDNA thus obtained to the downstream of a proper promoter (e.g., trp promoter, lac promoter, λ PL promoter, T7 promoter etc.), and then inserting it into a vector (e.g., pBR322, pUC18, pUC19 etc.) which functions in an *E. Coli* strain.

Then, an *E. Coli* strain (e.g., *E. Coli* DH5α strain, *E. Coli* JM109 strain, *E. Coli* HB101 strain, etc.) which is transformed with the expression vector described above may be cultured in an appropriate medium to obtain the desired polypeptide. When a signal peptide of bacteria (e.g., signal peptide of pel B) is utilized, the desired polypeptide may be also released in periplasm. Furthermore, a fusion protein with other polypeptide may be also produced readily.

In the expression of the polypeptide, for example, in a mammalian cells, for example, the expression vector may be prepared by inserting the cDNA encoding nucleotide sequence shown in SEQ ID NO. 3 into the downstream of a proper promoter (e.g., SV40 promoter, SRα promoter, LTR promoter, metallothionein promoter etc.) in a proper vector (e.g., retrovirus vector, papilloma virus vector, vaccinia virus vector, SV40 vector, etc.). A proper mammalian cell (e.g., human undifferenciated eosinophilic leukemia EOL cell, COS-7 cell, CHO cell, mouse L cell etc.) is transformed with the expression vector thus obtained, and then the transformant is cultured in a proper medium to express the aimed polypeptides. Thus obtained polypeptides may be isolated and purified with the known biochemical methods.

INDUSTRIAL UTILITY

RelA-associated inhibitor (polypeptides) of the present invention is capable of binding to p65 in nucleus, which is a submit of transcription factor NFκB, and inhibiting activity of NFκB and transcription of gene in nucleus. Therefore, it is useful for treatment and/or prevention of adult respiratory distress syndrome (ARDS), asthma, Allograft rejection, inflammatory diseases (inflammatory arthritis, angitis etc.), ischemic diseases, autoimmune diseases (especially, AIDS), metastasis and invasion of cancer, vasoreconstriction and diseases induced by NFκB besides the above. Further, it also relates to cardiogenesis and suppression of cardiac inflammation, so it may be used for regenerating cardiomuscle cells.

In addition, the antibody of the present invention may be used for diagnosis of the above diseases.

A pharmaceutical composition comprising RelA-associated inhibitor, antibody against it or antisence thereof of t he present invention and pharmaceutically acceptable diluent and/or a carrier is also included in the present invention.

RelA-associated inhibitor, cDNA encoding it, antibody against it and antisense of the present invention may be administered as solid compositions, liquid compositions or other compositions for oral administration, as injections, liniments or suppositories etc. for parental administration.

Solid compositions for oral administration include compressed tablets, pills, capsules, dispersible powders, and granules. Capsules include soft or hard capsules.

The doses to be administered depend upon age, body weight, symptom, desired therapeutic effect, route of administration, and duration of the treatment etc. In human adults, one dose per person is generally between 100 μg and 100 mg, by oral administration, up to several times per day, and between 10 μg and 100 mg, by parental administration up to several times per day.

As mentioned above, the doses to be used depend upon various conditions. Therefore, there are cases in which doses lower than or greater than the ranges specified above may be used.

The antibody against RelA-associated inhibitor of the present invention may be used for diagnosis of the above diseases.

An quantitative assay of RelA-associated inhibitor of the present invention in the body may be carried out using polychlonal or monoclonal antibody against it. Based on the assay, it is possible to study the relationship between RelA-associated inhibitor of the present invention and diseases or diagnose such diseases.

Polyclonal and monoclonal antibodies can be prepared using the polypeptide of the present invention or its fragment as an antigen by conventional methods. Further, purification or gene cloning of proteins (NFκB) capable of binding to the RelA-associated inhibitor (polypeptide) can be performed using the present polypeptide. In addition, the present polypeptide may be used for screening RelA-associated inhibitor agonist or antagonist.

cDNAs of the invention are useful as not only the important and essential template for the production of the RelA-associated inhibitor of the invention which is expected to be largely useful, but also be useful for diagnosis or therapy (for example, treatment of gene lacking, treatment to stop the expression of the RelA-associated inhibitor by antisense DNA (RNA)). Genomic DNA may be isolated using the cDNA of the invention, as a probe. As the same manner, a human gene encoding which can be highly homologous to the cDNA of the invention, that is, which encodes a polypeptide highly homologous to the RelA-associated inhibitor of the invention and a gene of animals excluding human which can be highly homologous to the cDNA of the invention, also may be isolated.

BEST MODE CARRYING OUT THE INVENTION

The invention is illustrated by the following Examples and Reference Examples, but not limit the invention.

EXAMPLE 1

Construction of Plasmids-Plasmids

Construction of plasmids-plasmids were constructed by standard methods.

The human p65 (amino acids 176–405) fragment was cloned into pAS2-1 (Clontech Co., Palo Alto) by the yeast two-hybrid system.

PCR amplification using 5' and 3' oligonucleotides containing BamHI restriction sites, i.e., Forward: 5'-GGCGGATCCCTCCGCCTGCCGCCTGTC-3' (SEQ ID NO. 5), and Reverse: 5'-GCTGGATCCGGGGCAGGGGCTGGAGCC-3' (SEQ ID NO. 6) was carried out. The resulting plasmid was named pAS2-1-p65 (176–405). pACT2-p35, encoding the largest RelA Associated Inhibitor (hereinafter abbreviated as RAI) insert obtained from library screening, was cut with EcoRI and XhoI. This EcoRI-XhoI fragment was purified and cloned into EcoRI-XhoI-digested vector pGEX-5X-2 (Pharmacia Co.).

RAI cDNA was cloned as described below.

The full length RAI was amplified using the oligonucleotides containing SalI and BamHI restriction sites, i.e., Forward: 5'-CAATGGTCGACATGGATCTGACTCTTGCTG-3' (SEQ ID NO. 7) and Reverse: 5'-GATCAGGATCCTCAGGCCAAGCTCCTTTGT-3' (SEQ ID NO. 8) respectively, and cloned as a SalI-BamHI fragment into plasmid pEGFP-C1 to obtain plasmid pEGFP-RAI which may produce fusion protein with RAI in frame with GFP.

pEGFP-RAI (1–146) was prepared from pEGFP-RAI by cutting with BssHII and BamHI, blunt ended with Klenow enzyme and cloning into pEGFP-C1.

The pEGFP-RAI (132–351) was prepared by amplifying the corresponding RAI fragment by PCR using the oligonucleotides F132 containing EcoRI and BamHI sites, ie., Forward: 5'-GCTTCGAAT TCTGTGCTGCGGAAGGCG-3' (SEQ ID NO. 9) and Reverse: 5'-GATCAGGATCCT-CAGGCCAAGCTCCTTTGT-3' (SEQ ID NO. 10) respectively, and by cloning into pEGFP-C1. pFLAG-CMV-RAI was prepared by inserting the full-length RAI fragment from pEGFP-RAI into SalI and BamHI restriction sites of pFLAG-CMV-2 vector.

All the PCR were carried out using Expand high fidelity system (Boehringer Mannheim Co.).

All the constructs were confirmed by dideoxynucleotide sequencing using ABI PRISM dye terminator cycle sequencing ready reaction kit (Perkin Elmer Co.).

Plasmids PG13-Luc containing a generic p53 response element, and pCMV-p53wt expressing wild type human p53, were generous gifts from Dr. B. Vogelstein. The constructions of 4kBw-Luc and 4kBm-Luc have been carried out by known methods described in articles.

Yeast two-hybrid screen—pAS2-1-p65 (176–405) was used as probe to screen human placenta and brain cDNA libraries according to the Matchmaker Two-Hybrid System protocol (Clontech Co.). Positive yeast clones were selected by prototrophy for histidine and by expression of β-galactosidase. Library derived from plasmids were rescued from positive clones and transformed into E. coli HB101.

Subsequent two-hybrid assays were carried out by introducing the plasmids into yeast strain Y187 carrying a Gal1-regulated reporter gene and detected the expression of β-galactosidase to confirm the specific binding.

Plasmids containing cDNA clones that specifically interact with p65 (176–405) were identified by restriction mapping, PCR using gene specific primers, and DNA sequencing of both strands.

Sequence Network BLAST searches were conducted by using the National Center for Biotechnology Information (NCBI) on-line service.

EXAMPLE 2

Culturing Cell and Transfection

HeLa, 293T and Saos-2 and COS-1 cells were incubated at 37° C. in Dulbecco's modified Eagle's medium with 10% heat-inactivated fetal bovine serum (FBS), 1 mM glutamate, 100 U/ml penicillin, and 100 mg/ml streptomycin. Jurkat human T cells were maintained in RPMI 1640 with 10% FBS plus antibiotics.

Cells were transfected using SuperFect transfection reagent (Qiagen Co.) according to the manufacturer's recommendations.

EXAMPLE 3

Purification and Expression of Recombinant Proteins pGEX-5X-2 plasmid encoding glutathione S-transferase (GST)-fusion proteins were transformed in E. coli strain BL21 (DE3) pLysS following induction with isopropyl-1-thio-β-D-galactopyranoside (IPTG, 0.1 mM) at 28° C. overnight. Recombinant GST-fusion proteins were purified by incubating the bacterial extracts in buffer A (Tris-HCl (pH 7.4; 50 mM), DTT (1 mM), EDTA (1 mM), EGTA (0.1 mM), NaCl (100 mM), benzamidine (1 mM), phenylmethylsulphonyl fluoride (PMSF) (0.1 mM), tosylphenylalanylchloromethylketone (0.1 mM), 0.25% (v/v) Nonidet P-40 (NP-40)) with glutathione-sepharose beads (Pharmacia Biotech Co.).

The beads were washed five times with ice-cold buffer A and suspended in buffer A (1 ml). The purification and examination of quantity of bound GST fusion proteins were carried out by SDS-PAGE using 5–20% sodium dodecyl sulfate-polyacrylamide and by stain using Coomassie brilliant blue.

EXAMPLE 4

In Vitro Assays $^{35}$S-methionine-labeled p65 was synthesized by using the TNT T7/SP6 wheat germ extract coupling system (Promega Co.) according to the manufacturer's protocols.

For in vitro protein-protein interaction studies, an equal amount of the in vitro-translated $^{35}$S-methionine-labeled p65 was incubated with 5 mg of purified GST-RAI fusion proteins or GST alone (as a negative control) that were bound to glutathione-sepharose beads at 25° C. for 1 h in buffer A (250 ml).

The beads were washed by resuspension and centrifugation five times with 1 ml of ice-cold binding buffer A containing 0.1% NP-40. Bound proteins were eluted with an equal volume of SDS loading buffer, boiled for 3 min, dissolved into 5–20% SDS-PAGE, and visualized by autoradiography.

EXAMPLE 5

Isolation of Full-Length RAI

A fragment encoding the longest RAI obtained from yeast two-hybrid screen was used as a hybridization probe to screen a human placenta 5'-STRETCH PLUS cDNA library (Clontech Co.). The probe was labeled by $^{32}$P using Prime-It Random Primer Labeling Kit (Stratagene). Hybridization was performed according to the manufacturer's recommendations. The filters were washed to a final stringency of 0.1×SSC-0.5% SDS at 65° C. and exposed to X-ray film (X-Omat AR; Eastman Kodak Co.) overnight with intensifying screens. The films were developed and plaques hybridizing on filters were identified and isolated. Phages were eluted from agarose plugs in SM buffer and stored at 4° C. (primary plaque pools). Secondary and tertiary plaque purifications were performed in similar fashion to that for the primary pools and a series of such procedures was repeated until single plaques could be isolated.

EXAMPLE 6

Western Blotting

Full-length RAI was cloned into a CMV promoter expression vector designed to place a FLAG epitope tag at the 5' end of the open reading frame. 293T cells were transfected using SuperFect transfection reagent as described above. Proteins were isolated from extraction of whole cells in a SDS-containing buffer. Western blotting was performed by a standard technique, using anti-FLAG antibody (Santa Cruz Co.) at a dilution of 1/1,000. Secondary antibody, horseradish peroxidase-conjugated anti-rabbit IgG antibody was used at a dilution of 1/2,500, and protein bands were visualized by enhanced chemiluminesacence (Amersham Co.).

EXAMPLE 7

Co-Immunoprecipitation

After transfection, 293T cells were cultured for 24 hour and then harvested (proliferated). After washing with PBS, cells were lysed in 350 ml ice-cold lysis buffer (Tris HCl (pH 7.4; 50 mM), 150 mM NaCl, 2 mM EDTA, 1 mM PMSF, 1 mM DTT, 0.2% NP-40, 10 mM NaF, 10µg/ml aprotinin, 10 by centrifugation. The supernatants were incubated with anti-FLAG M2 murine monoclonal antibody (Kodak Co.) or control mouse monoclonal antibody (Dako Co.) or rabbit polyclonal IκB-α antibody (Santa Cruz Co.) overnight at 4° C. and then with protein A-Sepharose (Pharmacia Co.) for 4 h. The beads were washed six times with 1 ml lysis buffer. Bound proteins were eluted with an equal volume of SDS loading buffer and resolved on 10% SDS-PAGE. Western blot was conducted as described above using anti-NF-κB p65 (C-20) antibody (Santa Cruz Co.).

EXAMPLE 8

Northern Blot Hybridization

Northern blot hybridization of the human multiple tissue blots (Clontech Co.) was performed according to the manufacturer's recommendations. A full-length of RAI cDNA was used as a probe. The blots were also probed with an β-actin fragment to confirm that equal amount of RNAs was blotted.

EXAMPLE 9

Microscopic Examination

HeLa cells were cultured in 4-well chamber slides and transfected with plasmids expressing various GFP fusion proteins using SuperFect transfection reagent (Qiagen Co.). After 24 h, cells were fixed by reacting in 4% paraformaldehyde for 15 min and stained with the DNA-binding dye Hoechst-33342 at room temperature for 15 min followed by washing in phosphate-buffered saline (PBS). The intracellular locations were examined by fluorescence microscopy.

EXAMPLE 10

Immunofluorescence Microscopy pEGFP-RAI (0.1 mg) was transfected into HeLa cells cultured in 4-well chamber slides. Twenty-four hour after transfection, cells were untreated or treated with 10 ng/ml TNF-α, then were immuno-stained according to the methods described as hereinbefore. Briefly, cells were fixed with 4% (w/v) paraformaldehyde/PBS for 10 min at room temperature and then were permeabilized by 0.5% Triton X-100/PBS for 20 min at room temperature. They were then incubated with rabbit polyclonal antibody against p65 (Santa Cruz Co.) for 1 h at 37° C. After washing with PBS, the cells were incubated with TRITC-conjugated goat anti-rabbit IgG antibody (Cappel Organon Teknika Co.) for 30 min at 37° C. Then the cells were stained with Hoechst-33342 at room temperature for 15 min to view the nuclear morphology. The slides were examined by fluorescence microscopy.

EXAMPLE 11

Luciferase Assay

HeLa and Saos-2 cells were cultured in 12-well plates and transfections were performed with SuperFect transfection reagent (Qiagen Co.). For each transfection, 50 ng of KB-dependent or mutant reporter plasmid (4kBw-Luc or 5kBm-Luc) or 250 ng of p53-dependent luciferase reporter plasmid (PG13-Luc) and 30 ng of internal control plasmid pRL-TK were used. The empty vector pEBVHisB or pFLAG-CMV-2 was used to adjust the total amount of DNA transfected to 1.5 µg. Twenty-four hours post-transfection, cells were harvested to measure the luciferase activity (Sato, T et al, AIDS Res. Hum. retrovir. 14, 293–298 (1998)). Jurkat cells were transfected with indicated plasmids. Twenty-four hour post-transfection, the cells were induced by 5 ng/ml TNF-α for 24 h and harvested for luciferase assay.

EXAMPLE 12

Gel Electrophoretic Mobility Shift Assay 293T cells were transfected for 24 h and nuclear extracts were prepared according to the known methods described previously (Okamoto, T, et al, Virology 177, 606–614 (1990)). The nuclear pellet was lysed in 35 ml of extraction buffer (50 mM HEPES, pH 7.4, 50 mM KCl, 350 mM NaCl, 0.1 mM EDTA, 1 mM DTT, 0.1 mM PMSF, 10% glycerol).

The protein content was measured by the DC protein Assay (Bio-RAD Co.). The gel electrophoretic mobility shift assay (EMSA) was performed according to the known methods described previously (Yang, J. -P., et al, FEBS Lett. 361, 89–96 (1995): Liu, Z. -Q., et al, FEBS Lett. 385, 109–113 (1996)) using the kB sequence taken from the human immunodeficiency virus LTR. As a control, Oct-consensus olignucleotide: 5'-TGTCGAATGCAAATCAC-TAGAA-3' (SEQ ID NO. 11) was used. Oligonucleotides were labeled using DNA polymerase Klenow fragment (Takeda Biomedicals Co.) and [α-$^{32}$P]dATP (3000 Ci/mmol, ICN Pharmaceuticals Inc.).

DNA binding reactions were performed at room temperature for 15 min in 10-µl reaction voluminous containing 5 µg of nuclear extracts. Analysis of binding complexes was performed by electrophoresis in 5% native polyacrylamide gels with 0.5×tris-borate-EDTA buffer, followed by autoradiography. For DNA competition experiments, unlabeled competitor oligonuclotides were added into the reaction mixture at 50-fold molar excess over the probe.

RESULTS

Isolation of RAI cDNA Clones as a p65-Binding Protein

The yeast two-hybrid system has been employed to identify proteins that interact with p65. DNA fragment encoding amino acids (176–405) of p65, which contained the dimerization domain, nuclear localization signal and the proline-rich motif, was cloned into pAS2-1 containing a DNA-binding domain of yeast GAL4 in frame. The resulting plasmid, pAS2-1-p65 (176–405), was used as a probe to screen human cDNA libraries (placenta and brain) that had been constructed in GAL4 transcriptional activation domain vector pACT2. The yeast strain Y190 was used for screening. From approximately 1.56×10$^6$ Y190 yeast transformants, 78 colonies grew on selective medium and turned blue when tested in a filter lift galactosidase assay.

Resulting from re-screening using Yeast strain Y187, 63 of plasmid clones encoding the proteins which specifically interacted with the p65 bait were found. These clones were then characterized by DNA sequence analysis of both strands.

Primary nucleotide sequencing revealed that in addition to those already identified as p65-binding proteins, such as genes encoding IκB-β/Trip9 (4 clones), p50/p105 (3 clones), p65/RelA (2 clones), c-Rel (1 clone) and 53BP2 (2 clones), four clones of an unidentified gene encoding a protein not previously described in the GenBank database were isolated (all of them were derived from human placenta cDNA library).

The present inventor has called this new protein RelA Associated Inhibitor (RAI). These four clones identified by the two-hybrid screen shared the same 3' end, but contained different insert sizes.

To confirm the direct interaction between p65 and RAI, in vitro binding assay between recombinant RAI and p65 proteins was performed. The cDNA insert from plasmid pACT2-RAI was cloned in frame into the GST expression plasmid for production of the GST-RAI fusion protein.

The GST fusion proteins were expressed in *E. coli* and purified by glutathione-sepharose beads (FIG. 1, lanes 1 and 2).

[$^{35}$S]methionine-labeled p65 was synthesized by in vitro transcription and translation protocol using wheat germ extract (FIG. 1, lane 3).

The purified GST-fusion proteins bound to glutathione-sepharose beads were incubated with the in vitro synthesized p65 protein. The beads were washed and bound material was analyzed by SDS-PAGE followed by autoradiography. As shown in FIG. 1, p65 interacted strongly with RAI (lane 5). Binding between p65 and RAI was considered as specific because no interaction of p65 was observed with the control GST protein (lane 4).

EXAMPLE 13

Isolation of Full-Length RAI

The four independent clones isolated from the yeast two-hybrid screen were partial-length cDNA derived from the same gene. Plaque hybridization of a human placenta cDNA library with the partial cDNA fragment of RAI isolated from the two-hybrid screen was performed to obtain a full-length clone. About $10^6$ plaques were screened. Nine cDNA clones were isolated with approximately 1 kb to 6 kb in length. Two longest cDNAs were sequenced on both strands and were found to contain the complete open reading frame (ORF) for RAI. The clones differed at their 5' end, and each contained all of the sequences present in pACT2-RAI. Both contained Alu repeat element in their 5' untranslated regions. The likely translation initiation codon of RAI was preceded by an in-frame stop codon located 27 bp upstream. Although the nucleotide sequence 5' of the first ATG (CTG-GCGATG) does not resemble the consensus initiation sequence, the present inventor designated this ATG as the putative translation start site. DNA sequence analysis revealed an open reading frame predicted to encode a putive protein of 351 amino acid residues with a predicted molecular mass of 40 kDa. Interestingly, a BLAST search revealed that the C-terminal of this protein has extensive homology to the C-terminal region of 53BP2, previously reported as p53 binding protein in a yeast two hybrid screen (Iwabuchi, K. et al, Proc. Natl. Acad. Sci. USA 91, 6098–6102 (1994)).

RAI protein was predicted to contain four consecutive ankyrin repeats (145 Arg-174 Asn, 176 Pro-207 Ala, 209 Val-241 Ala, 243 Phe-275 Glu) and an SH3 domain (287 Tyr-388 Phe) at its C-terminus as that of 53BP2, with 52% amino acid identity with 53BP2 at the C-terminal of 223 amino acid residues.

Apart from the ankyrin repeats and SH3 domain, the RAI sequence is unrelated to that of any protein in current databases using BLAST research.

EXAMPLE 14

Tissue Distribution of RAI in Human Tissues

Figure 2:
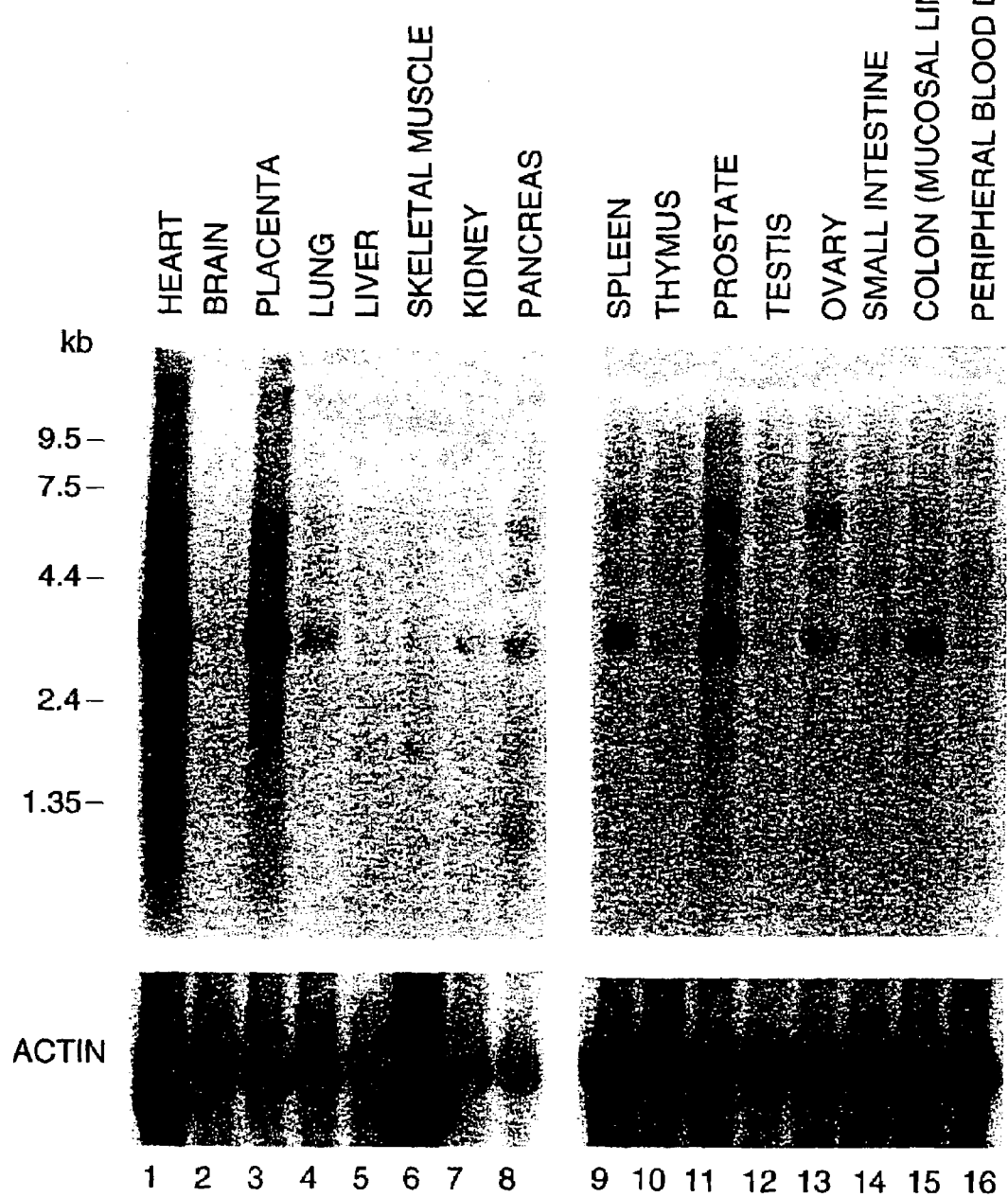
FIG. 2 shows the results of Northern blot analyses of RAI mRNA expression in human multiple tissues. The lower shows an amount of β-actin expression.

To determine the expression pattern of RAI, present inventor performed a Northern blot analysis on a human multi-tissue blot. As shown in FIG. 2, the RAI mRNA was detected as an approximately 3.4-kb and 6.0-kb band in most cases. From FIG. 2 clearly, the expression of RAI mRNA was significantly high in human heart, placenta and prostate while it was markedly reduced in liver, skeletal muscle, testis and peripheral blood leukocyte.

EXAMPLE 15

Inhibitory Action of RAI on NFκB-Dependent Transactivation

Since RAI was shown to bind p65 through its ankyrin repeats and SH3 domain as similarly to IκB family proteins, the present inventor confirmed whether RAI had any effect on the kB-dependent transcriptional activation. The luciferase reporter plasmid containing four tandem copies of the kB sequence was co-transfected into 293 T cells with an expression vector for FLAG-RAI and/or p65 expression vector. Twenty-four hours after transfection, luciferase activities were determined. As shown in FIG. 3, co-transfected p65-expressing plasmid as an activator strongly transactivated the reporter gene (FIG. 3, lane 9). Co-transfection with the RAI expressing plasmid resulted in the inhibition of the p65-induced NF KB activity in a dose-dependent manner. Although to a lesser extent, the inhibitory effect of RAI on the basal level of kB-dependent luciferase expression was observed (FIG. 3, lanes 11, 13 and 15).

The invention claimed is:

1. A substantially pure polypeptide comprising the amino acid sequence represented by SEQ ID NO:1.

* * * * *